United States Patent [19]
Diaz

[11] Patent Number: 5,690,674
[45] Date of Patent: Nov. 25, 1997

[54] WOUND CLOSURE WITH PLUG

[75] Inventor: Roberto Diaz, Miami, Fla.

[73] Assignee: Cordis Corporation, Miami Lakes, Fla.

[21] Appl. No.: 674,442

[22] Filed: Jul. 2, 1996

[51] Int. Cl.$^6$ ................................................. A61B 17/08
[52] U.S. Cl. ........................ 606/213; 606/215; 604/285
[58] Field of Search .................................. 606/213, 215;
600/32; 604/285, 286; 128/899, 831, 843

[56] References Cited

U.S. PATENT DOCUMENTS

| | | |
|---|---|---|
| 4,587,969 | 5/1986 | Gillis . |
| 4,744,364 | 5/1988 | Kensey . |
| 4,852,568 | 8/1989 | Kensey . |
| 4,890,612 | 1/1990 | Kensey . |
| 4,929,246 | 5/1990 | Sinofsky . |
| 5,021,059 | 6/1991 | Kensey et al. . |
| 5,041,129 | 8/1991 | Hayhurst et al. . |
| 5,053,046 | 10/1991 | Janese . |
| 5,061,274 | 10/1991 | Kensey . |
| 5,108,420 | 4/1992 | Marks ........................ 606/213 |
| 5,108,421 | 4/1992 | Fowler . |
| 5,129,882 | 7/1992 | Weldon et al. . |
| 5,149,331 | 9/1992 | Ferdman et al. . |
| 5,192,301 | 3/1993 | Kamiya et al. ............. 606/213 |
| 5,203,787 | 4/1993 | Noblitt et al. . |
| 5,221,259 | 6/1993 | Weldon et al. . |
| 5,222,974 | 6/1993 | Kensey et al. . |
| 5,254,133 | 10/1993 | Seid ............................ 606/215 |
| 5,292,332 | 3/1994 | Lee . |
| 5,334,217 | 8/1994 | Das ............................. 606/213 |
| 5,437,292 | 8/1995 | Kipshidze et al. . |
| 5,443,481 | 8/1995 | Lee . |
| 5,571,181 | 11/1996 | Li ................................ 623/11 |

FOREIGN PATENT DOCUMENTS

| | | |
|---|---|---|
| 0482350 | 4/1992 | European Pat. Off. . |
| 92/22252 | 12/1992 | WIPO . |

OTHER PUBLICATIONS

Ernst, S.M.P.G., et al., "Immediate Sealing of Arterial Puncture Sites After Cardiac Catheterization and Coronary Angioplasty Using a Biodegradable Collagen Plug: Results of an International Registry," *Journal of American College of Cardiology (JACC)*, vol. 21, No. 4, pp. 851–855 (Mar. 15, 1993).

Gibbs, J.S.R., et al., "Femoral Arterial Hemostasis Using a Collagen Plug After Coronary Artery Stent Implantation," *Journal of Interventional Cardiology*, vol. 5, No. 2, pp. 85–88 (1992).

Kensey, K.R., "Puncture Site Hemostasis," *The Journal of Invasive Cardiology*, vol. 6, No. 8, pp. 273–276 (Oct. 1994).

Kiemeneij, F., et al., "Improved Anticoagulation Management After Palmaz Schatz Coronary Stent Implantation by Sealing the Arterial Puncture Site with a Vascular Hemostasis Device," *Catheterization and Cardiovascular Diagnosis*, vol. 30, pp. 317–322 (1993).

(List continued on next page.)

*Primary Examiner*—Michael Buiz
*Assistant Examiner*—Tina T. D. Pham
*Attorney, Agent, or Firm*—Watts, Hoffmann, Fisher & Heinke, Co., L.P.A.

[57] ABSTRACT

An elastic, biodegradable plug has a proximal retainer and a distal retainer coupled by a waist. The plug may be positioned to straddle a wound in a blood vessel wall of a patient and therefore close the wound to stop bleeding through the wound. To position the plug in the wound, an operator may insert the plug into a sleeve extending through the vessel wall into the vessel and move the plug through the sleeve with a positioning tool. In the sleeve, the distal and proximal retainers of the plug are compressed. As the distal retainer of the plug exits the distal end of the sleeve into the vessel, the distal retainer expands in the vessel such that a surface of the distal retainer faces an inner side of the vessel wall. The positioning tool and the sleeve are then removed to position the waist in the wound of the vessel wall and allow the proximal retainer to expand such that a surface of the proximal retainer faces an outer side of the vessel wall.

9 Claims, 3 Drawing Sheets

OTHER PUBLICATIONS

Schräder, R., et al., "Collegen Application for Sealing of Arterial Puncture Sites in Comparison to Pressure Dressing: A Randomized Trial," *Catheterization and Cardiovascular Diagnosis*, vol. 27, pp. 298–302 (1992).

"FDA Suspends Review of Datascope Applications," newsclip, one sheet.

Slaughter, P.M.P., et al., "A Single Center Randomized Trial Assessing Use of a Vascular Hemostasis Device vs. Conventional Manual Compression Following PTCA: What Are the Potential Resource Savings?" *Catheterization and Cardiovascular Diagnosis*, vol. 34, pp. 210–214 (1995).

Spokojny, A.M., et al. "Management of the Arterial Puncture Site," *Journal of Interventional Cardiology*, vol. 7, No. 2, pp. 187–193 (1994).

"Tinel® Shape–Memory Alloys," Raychem Corporation, Menlo Park, CA, 11 sheets (1993).

"Kensey Nash Angio–Seal and Datascope Vasoseal are Approvable, FDA Advisory Panel Concludes; Warnings About High Risk Groups Must be in Labeling," M–D–D–I Reports—The Gray Sheet, F–D–C Reports, Inc., pp. 8–10 (May 15, 1995).

"Puncture Closure Devices Recommended for US Approval", newsclip, one sheet.

5,690,674

WOUND CLOSURE WITH PLUG

1. Field of the Invention

The present invention relates generally to the field of medical surgery. More particularly, the present invention relates to the field of vessel incision or wound closure.

2. Background of the Invention

Some medical procedures require surgical access into the vascular system of a patient through the wall of a blood vessel to accommodate a catheter sheath introducer. Medical instruments such as guidewires, catheters, and balloon angioplasty devices are inserted into the vascular system through the catheter sheath introducer to perform the medical procedure.

The catheter sheath introducer leaves in the vessel wall an incision or wound having a size corresponding to the outer diameter of the catheter sheath introducer at its distal end. After completion of the medical procedure, the wound must be closed to stop bleeding from the vessel. Direct pressure may be applied to the wound to stop the bleeding. The application of pressure to the wound, however, requires the dedication of time by medical personnel to assure the wound has closed and the bleeding has stopped. The continued application of pressure to the wound also undesirably restricts the flow of blood through the vessel and may lead to thrombosis for example.

SUMMARY OF THE INVENTION

A plug for closing a wound in a wall of a vessel comprises a first retainer having a surface, a second retainer having a surface, and a waist. The waist couples the first retainer and the second retainer such that the plug may be positioned to straddle the wound in the vessel wall with the waist positioned in the wound of the vessel wall, with the surface of the first retainer facing one side of the vessel wall, and with the surface of the second retainer facing an opposing side of the vessel wall to close the wound in the vessel wall.

The plug for one embodiment comprises an elastic, biodegradable material. The first retainer and the second retainer for one embodiment are each generally circular in shape, and the first retainer may have a diameter greater than that of the second retainer. The plug for one embodiment defines a socket extending through the first retainer into at least a portion of the waist for mating with a positioning tool to position the plug in the wound of the vessel wall.

A method for closing a wound in a wall of a vessel comprises the steps of compressing a distal retainer of a plug, inserting the distal retainer of the plug through the wound of the vessel wall into the vessel, and positioning a waist of the plug in the wound of the vessel wall such that the plug straddles the wound in the vessel wall with the distal retainer expanded in the vessel on an inner side of the vessel wall and with a surface of a proximal retainer of the plug facing an outer side of the vessel wall.

The plug for one embodiment comprises a biodegradable material. The proximal retainer and the distal retainer for one embodiment are each generally circular in shape, and the proximal retainer may have a diameter greater than that of the distal retainer.

The compressing step for one embodiment comprises the step of inserting the plug into a passageway of a sleeve such that the distal retainer and the proximal retainer are compressed in the passageway of the sleeve. The sleeve has a distal end extending through the vessel wall in the vessel. The sleeve for one embodiment is a catheter sheath introducer.

The inserting step for one embodiment comprises the step of moving the plug through the passageway of the sleeve such that the distal retainer exits the distal end of the sleeve and expands in the vessel. The method for one embodiment comprises the step of mating a positioning tool with a socket of the plug. The moving step for one embodiment comprises the step of pushing the plug through the passageway of the sleeve with the positioning tool until a predetermined location of the positioning tool reaches a proximal end of the sleeve.

The positioning step for one embodiment comprises the step of removing the sleeve from the vessel wall such that the proximal retainer expands.

Another method for closing a wound in a wall of a vessel comprises the steps of inserting a plug into a passageway of a sleeve having a distal end extending through the vessel wall into the vessel, moving the plug through the passageway of the sleeve until a distal retainer of the plug exits the distal end of the sleeve into the vessel, and positioning a waist of the plug in the wound of the vessel wall such that a surface of the distal retainer faces an inner side of the vessel wall and such that a surface of a proximal retainer of the plug faces an outer side of the vessel wall.

The plug for one embodiment comprises an elastic, biodegradable material. The sleeve for one embodiment is a catheter sheath introducer. The proximal retainer and the distal retainer for one embodiment are each generally circular in shape, and the proximal retainer may have a diameter greater than that of the distal retainer.

The method for one embodiment comprises the step of mating a positioning tool with a socket of the plug. The moving step for one embodiment comprises the step of pushing the plug through the passageway of the sleeve with the positioning tool until a predetermined location of the positioning tool reaches a proximal end of the sleeve.

BRIEF DESCRIPTION OF THE DRAWINGS

The present invention is illustrated by way of example and not limitation in the figures of the accompanying drawings, in which like references indicate similar elements and in which.

DETAILED DESCRIPTION

Figure 1:
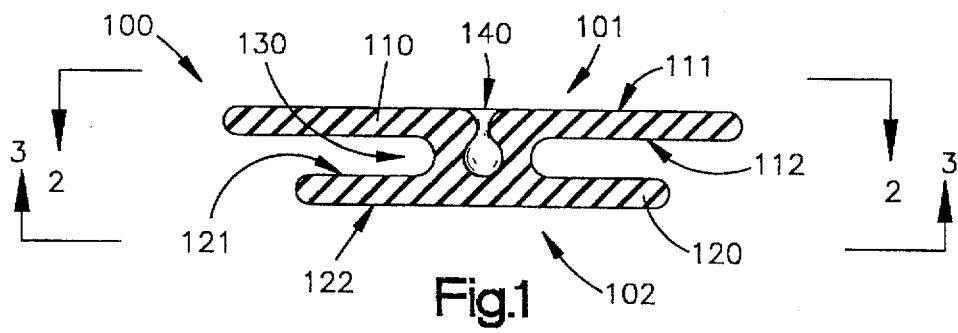
FIG. 1 illustrates a cross-sectional side view of a plug for one embodiment of the present invention.
Figure 2:
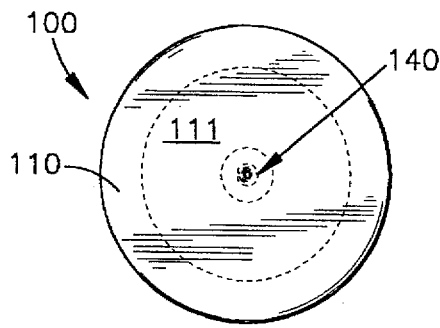
FIG. 2 illustrates a proximal end view of the plug seen approximately from the plane indicated by the line 2—2 of FIG. 1.
Figure 3:
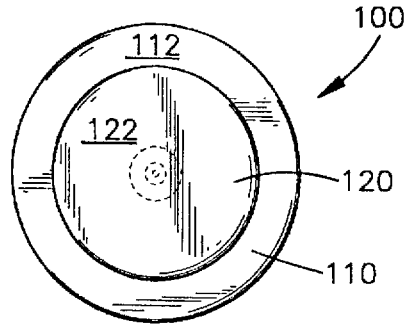
FIG. 3 illustrates a distal end view of the plug seen approximately from the plane indicated by the line 3—3 of FIG. 1.
Figure 10:
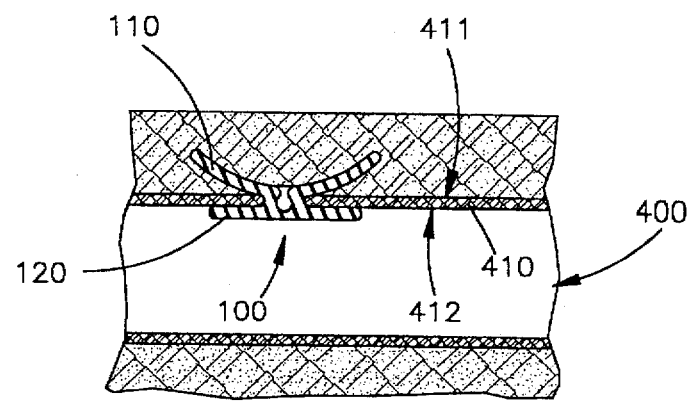
FIG. 10 illustrates a cross-sectional view of the plug positioned to close a wound of the vessel wall.

FIGS. 1, 2, and 3 illustrate a plug 100. The plug 100 may be inserted, for example, to plug or close a wound or incision in a wall 410 of a vessel 400 of a patient, as illustrated in FIG. 10. For one embodiment, an operator may position the plug 100 with a positioning tool 200, illustrated in FIG. 4, by inserting the plug 100 into and moving the plug 100 through a sleeve 300 with the positioning tool 200 to close the wound, as illustrated in FIGS. 5, 6, 7, 8, 9, and 10.

As illustrated in FIGS. 1, 2, and 3, the plug 100 has a proximal end 101 and a distal end 102. The plug 100 comprises a proximal retainer 110 at the proximal end 101 and a distal retainer 120 at the distal end 102. The plug 100 also comprises a waist 130 coupled between the proximal retainer 110 and the distal retainer 120. For one embodiment, the plug 100 is formed as an integral body defining the proximal retainer 110, the distal retainer 120, and the waist 130.

The plug 100 may be formed from any suitable elastic or resilient material. Preferably, the material for the plug 100 is biodegradable or capable of being absorbed by surrounding tissue when positioned in the patient. The plug 100 for one embodiment may comprise a suitable radiopaque material viewable with an x-ray imaging system to monitor the plug 100 as the plug 100 is positioned in the wound of the vessel wall 410 and while the plug 100 remains in the patient.

The proximal retainer 110 has a proximal surface 111 facing the proximal end 101 of the plug 100 and a distal surface 112 facing the distal end 102 of the plug 100. The distal retainer 120 has a proximal surface 121 facing the proximal end 101 of the plug 100 and a distal surface 122 facing the distal end 102 of the plug 100. The waist 130 couples the distal surface 112 of the proximal retainer 110 and the proximal surface 121 of the distal retainer 120 such that the distal surface 112 of the proximal retainer 110 faces the proximal surface 121 of the distal retainer 120. The proximal retainer 110, the distal retainer 120, and the waist 130 may have any suitable dimensions that may depend, for example, on the dimensions of the vessel 400, the vessel wall 410, the wound in the vessel wall 410, and the sleeve 300, for example.

For one embodiment, the proximal retainer 110 and the distal retainer 120 are each generally circular in shape. The proximal retainer 110 may have any suitable diameter, such as approximately 0.500 inch for example, and any suitable thickness, such as approximately 0.020 inch for example, from the proximal surface 111 to the distal surface 112. The distal retainer 120 may have any suitable diameter, such as approximately 0.312 inch for example, and any suitable thickness, such as approximately 0.010 inch for example, from the proximal surface 121 to the distal surface 122. For one embodiment, the diameter of the proximal retainer 110 is greater than the diameter of the distal retainer 120.

The waist 130 for one embodiment is generally cylindrical in shape and couples the proximal retainer 110 with the distal retainer 120 such that the proximal retainer 110, the distal retainer 120, and the waist 130 are generally aligned along a central axis. The waist 130 may have any suitable diameter, such as approximately 0.125 inch for example, and any suitable thickness, such as approximately 0.080 inch for example, from the distal surface 112 of the proximal retainer 110 to the proximal surface 121 of the distal retainer 120. The diameter of the waist 130 is preferably smaller than that of the proximal retainer 110 and that of the distal retainer 120.

As illustrated in FIG. 10, the waist 130 of the plug 100 couples the proximal retainer 110 and the distal retainer 120 such that the plug 100 may be positioned to straddle the wound in the vessel wall 410 with the waist 130 positioned in the wound of the vessel wall 410, with the distal surface 112 of the proximal retainer 110 facing an outer side 411 of the vessel wall 410, and with the proximal surface 121 of the distal retainer 120 facing an inner side 412 of the vessel wall 410 opposing the outer side 411. As the proximal retainer 110 and the distal retainer 120 are each larger in size than the wound in the vessel wall 410, the proximal retainer 110 and the distal retainer 120 help prevent the plug 100 from moving through the wound to the inside of the vessel 400 or to the outside of the vessel 400, respectively. In this manner, the plug 100 closes the wound and is secured in the wound to help prevent bleeding through the wound.

To position the plug 100 in the wound of the vessel wall 410, the distal retainer 120 may be compressed and inserted through the wound of the vessel wall 410. The waist 130 of the plug 100 may then be positioned in the wound of the vessel wall 410, allowing the distal retainer 120 to expand in the vessel 400 on the inner side 412 of the vessel wall 410.

Figure 4:
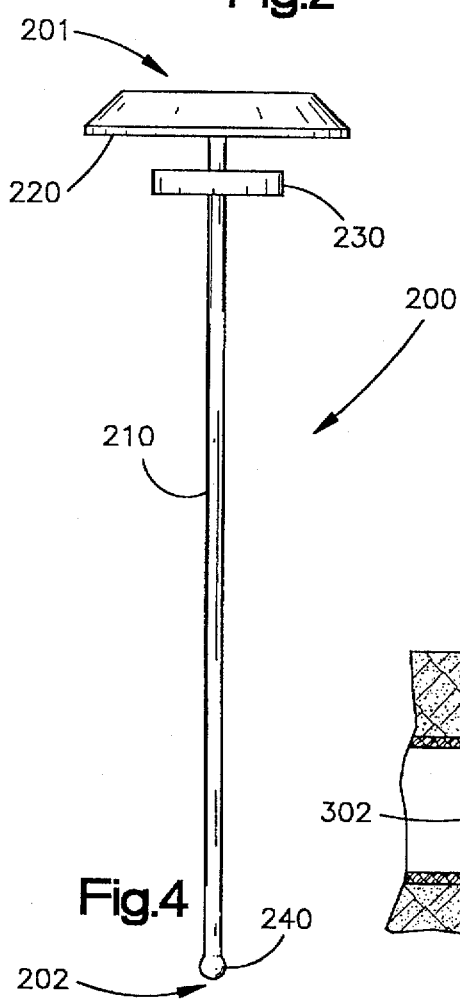
FIG. 4 illustrates a side view of a positioning tool for one embodiment of the present invention.

The plug 100 for one embodiment defines a socket 140 configured to mate with the positioning tool 200 of FIG. 4 to help position the plug 100 in the wound of the vessel wall 410. The plug 100 defines the socket 140 with a mouth at the proximal surface 111 of the proximal retainer 110. The socket 140 extends through the proximal retainer 110 toward the distal end 102 into at least a portion of the waist 130. For one embodiment, the socket 140 is generally aligned along the central axis of the plug 100 and is configured to form a ball-and-socket joint with the positioning tool 200.

The positioning tool 200 helps position the plug 100 in closing the wound in the vessel wall 410. The positioning tool 200 may be formed from any suitable material, such as a high density (HD) polyethylene for example. The positioning tool 200 for one embodiment may comprise a suitable radiopaque material viewable with an x-ray imaging system to help monitor the positioning of the plug 100 in the wound of the vessel wall 410.

As illustrated in FIG. 4, the positioning tool 200 has a proximal end 201 and a distal end 202. The positioning tool 200 comprises an elongate stem 210 extending from the proximal end 201 to the distal end 202 and comprises a knob 240 at the distal end 202. The knob 240 is configured to mate with the socket 140 of the plug 100.

The stem 210 may have any suitable dimensions and for one embodiment has a diameter of approximately 0.062 inch, for example, and a length of approximately 6 inches, for example, from the proximal end 201 to the distal end 202. For one embodiment, the knob 240 is generally spherical in shape and may have any suitable diameter, such as approximately 0.090 inch for example.

The positioning tool 200 for one embodiment also comprises a cap 220 and a stop flange 230. The cap 220 is coupled to the stem 210 at the proximal end 201 of the positioning tool 200. The stop flange 230 is coupled at a suitable position along the stem 210 and marks a predetermined location for the positioning tool 200. The position of the stop flange 230 along the stem 210 may depend, for example, on the length of the sleeve 300 of FIG. 5. The cap 220 and the stop flange 230 may have any suitable dimensions and for one embodiment are each generally circular in shape. For another embodiment, the cap 220 and the stop flange 230 are combined as one to form a stop flange capping the stem 210 at the proximal end 201 of the positioning tool 200.

Figure 5:
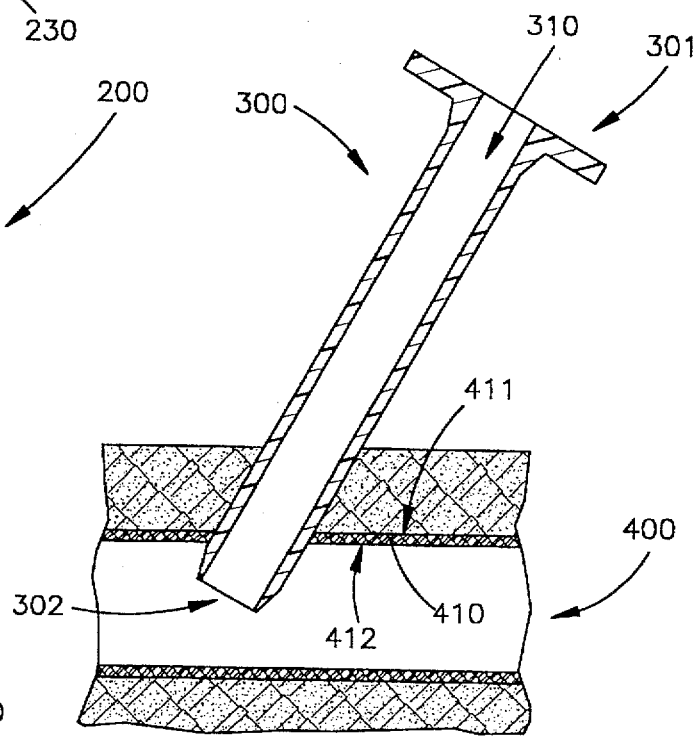
FIG. 5 illustrates a cross-sectional view of a sleeve having a distal end extending through a vessel wall.

As illustrated in FIGS. 5–10, the plug 100 may be inserted into and moved through the sleeve 300 with the positioning tool 200 to close the wound in the vessel wall 410. The sleeve 300, as illustrated in FIG. 5, has a proximal end 301 and a distal end 302 extending through the vessel wall 410. The sleeve 300 defines a passageway 310 extending through the sleeve 300 from the proximal end 301 to the distal end 302. For one embodiment, the sleeve 300 is generally cylindrical in shape.

The sleeve 300 for one embodiment is a catheter sheath introducer inserted through the vessel wall 410 to provide access for instruments, such as guidewires, catheters, and balloon angioplasty devices for example, through the passageway 310 into the vascular system of the patient to perform a desired medical procedure. Upon completion of the medical procedure, the plug 100 may be inserted into and moved through the sleeve 300 with the positioning tool 200 to plug the wound in the vessel wall 410 resulting from the insertion of the catheter sheath introducer through the vessel wall 410.

Figure 6:
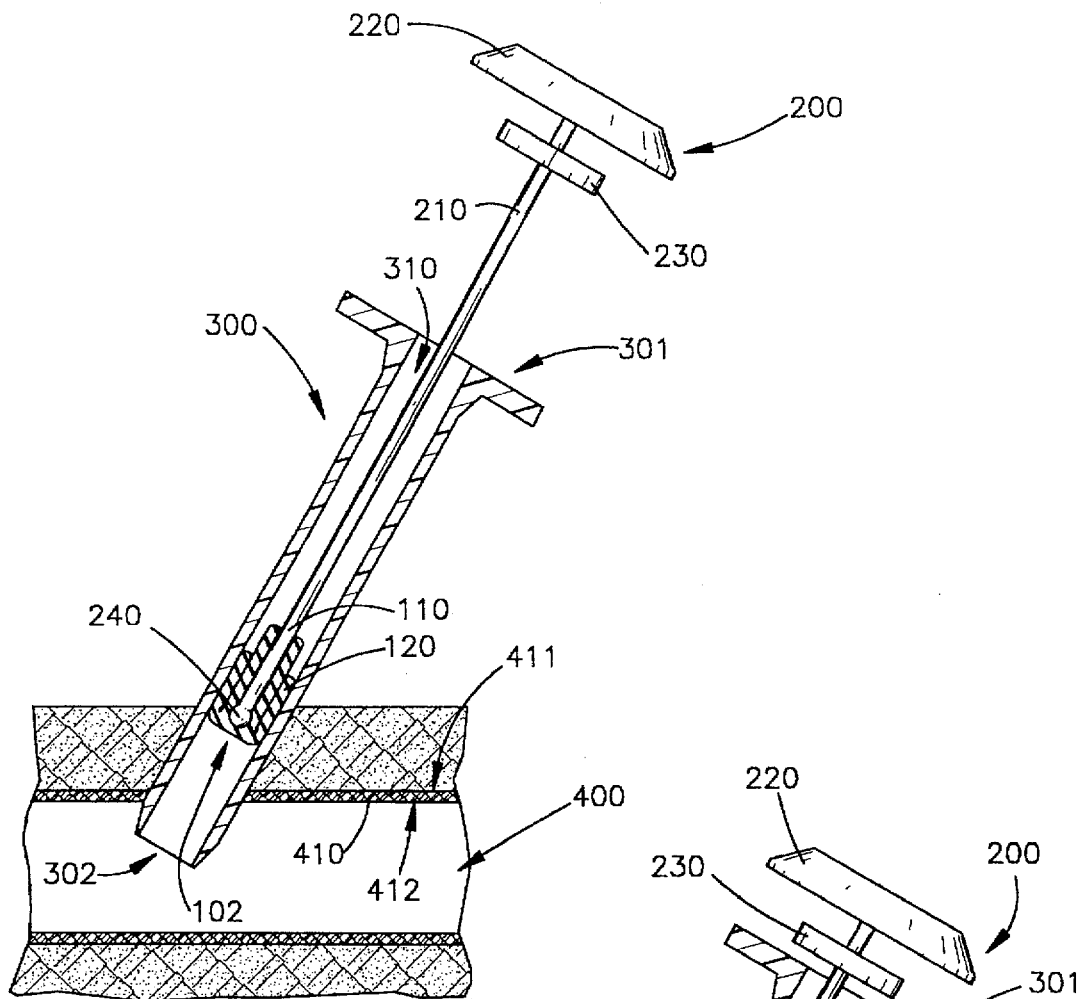
FIG. 6 illustrates a cross-sectional view of the sleeve of FIG. 5 with the positioning tool of FIG. 4 pushing the plug of FIG. 1 through the sleeve.

To insert the plug 100 through the sleeve 300, the knob 240 of the positioning tool 200 is mated with the socket 140 of the plug 100, and the distal end 102 of the plug 100 is inserted into the passageway 310 of the sleeve 300 such that the proximal retainer 110 and the distal retainer 120 are compressed by the passageway 310. As illustrated in FIG. 6, the passageway 310 bends the proximal retainer 110 and the distal retainer 120 back toward the proximal end 301 of the sleeve 300. In this compressed position, the distal retainer 120 flexes outward against the inner walls of the passageway 310, and the proximal retainer 110 may flex outward against at least a portion of the proximal surface 121 of the distal retainer 120. The plug 100 is pushed through the passageway 310 with the positioning tool 200 in this compressed position toward the distal end 302.

Figure 7:
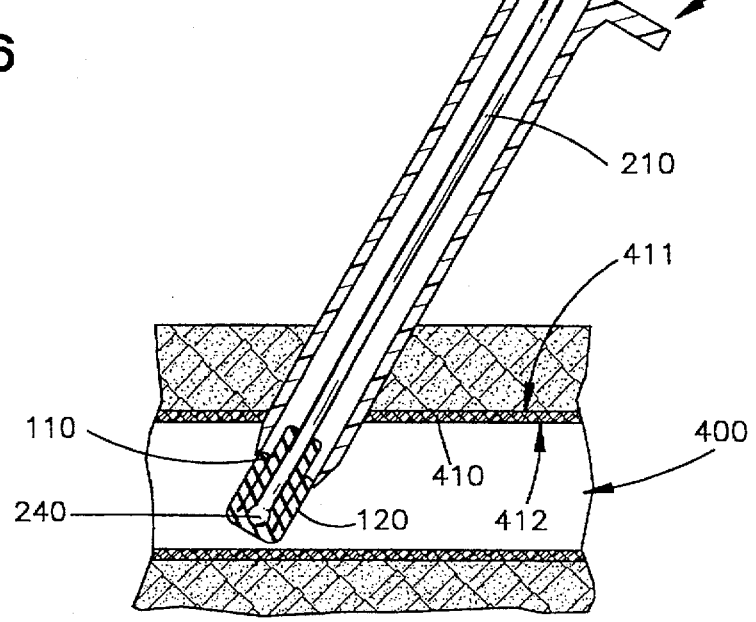
FIG. 7 illustrates a cross-sectional view of the sleeve with the positioning tool pushing the plug through the distal end of the sleeve.
Figures 8, 9:
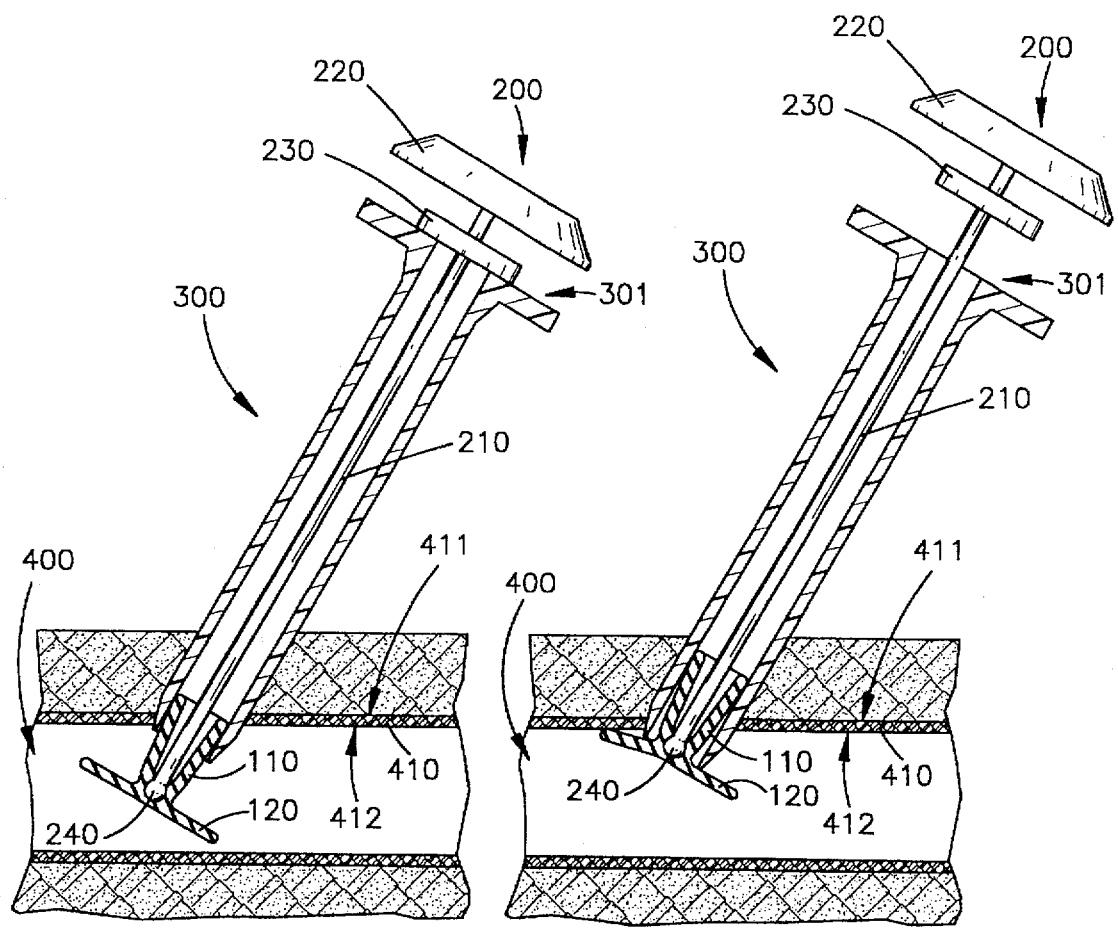
FIG. 8 illustrates a cross-sectional view of the sleeve with a distal retainer of the plug in an expanded position at the distal end of the sleeve.
FIG. 9 illustrates a cross-sectional view of the sleeve with the positioning tool pulling the expanded distal retainer of the plug toward the distal end of the sleeve.

The plug 100 is moved through the passageway 310 until the distal retainer 120 exits the passageway 310 at the distal end 302, as illustrated in FIGS. 7 and 8. The operator may determine the distal retainer 120 has exited the distal end 302 of the sleeve 300 when the predetermined location of the positioning tool 200 marked by the stop flange 230 reaches the proximal end 301 of the sleeve 300. As illustrated in FIG. 7, the stop flange 230 on the stem 210 of the positioning tool 200 nears the proximal end 301 of the sleeve 300 as the distal retainer 120 exits the passageway 310.

The stop flange 230 for one embodiment is wider than the passageway 310 so that the stop flange 230 abuts the proximal end 301 of the sleeve 300 and helps prevent the proximal retainer 110 from exiting the passageway 310 after the distal retainer 120 is pushed through the passageway 310 and expands in the vessel 400, as illustrated in FIG. 8. As the knob 240 continues to engage the socket 140 of the plug 100, the stop flange 230 helps prevent the operator from inadvertently pushing the entire plug 100 into the vessel 400.

As illustrated in FIG. 9, the plug 100 with the distal retainer 120 expanded at the distal end 302 of the sleeve 300 is pulled back toward the proximal end 301 of the sleeve 300 with the positioning tool 200. With the proximal surface 121 of the distal retainer 120 against the distal end 302 of the sleeve 300, the positioning tool 200 may be pulled to disengage the knob 240 from the socket 140 of the plug 100. The positioning tool 200 and the sleeve 300 may then be pulled and removed from the patient to position the plug 100 in the wound of the vessel wall 410. As the proximal retainer 110 expands upon removal of the sleeve 300, the plug 100 is positioned to straddle the wound in the vessel wall 410 as illustrated in FIG. 10.

The plug 100 may be left in place to close the wound once positioned in the vessel wall 410. Preferably, the plug 100 is formed from a biodegradable material so that the plug 100 is absorbed by surrounding tissue, allowing the vessel wall 410 itself to close the wound. As compared to the application of direct pressure to the wound, closure of the wound with the plug 100 helps minimize any restriction of blood flow through the vessel 400 as the distal retainer 120 occupies relatively minimal space in the vessel 400. Closure of the wound with the plug 100 therefore helps reduce the risk of bleeding complications, such as thrombosis for example. As the plug 100 closes the wound with minimized blood flow restriction once positioned in the vessel wall 410, closure of the wound with the plug 100 also helps minimize the dedication of time by medical personnel otherwise required to apply pressure to the wound, wait for the wound to close through blood clotting, and monitor the patient for bleeding complications.

In the foregoing description, the invention has been described with reference to specific exemplary embodiments thereof. It will, however, be evident that various modifications and changes may be made thereto without departing from the broader spirit or scope of the present invention as defined in the appended claims. The specification and drawings are, accordingly, to be regarded in an illustrative rather than a restrictive sense.

What is claimed is:

1. A method for closing a wound in a wall of a vessel, comprising the steps of:

a) mating a positioning tool with a plug comprising an elastic material;

b) inserting the plug into a passageway of a sleeve such that a distal retainer of the plug is compressed in the passageway of the sleeve, the sleeve having a distal end extending through the vessel wall in the vessel;

c) pushing the plug through the passageway of the sleeve with the positioning tool such that the distal retainer exits the distal end of the sleeve and expands in the vessel; and d) positioning the plug in the wound of the vessel wall, wherein the positioning step (d) comprises the step of pulling the expanded distal retainer against the distal end of the sleeve with the positioning tool to disengage the positioning tool from the plug.

2. The method of claim 1, wherein the positioning step (d) comprises the step of removing the sleeve from the vessel wall such that a proximal retainer of the plug expands to position the plug in the wound of the vessel wall with the distal retainer expanded in the vessel on an inner side of the vessel wall and with the proximal retainer expanded on an outer side of the vessel wall.

3. The method of claim 2, wherein the plug comprises a waist coupling the distal retainer and the proximal retainer and wherein the plug is positioned to straddle the wound in the vessel wall with the waist positioned in the wound of the vessel wall, with a surface of the distal retainer facing the inner side of the vessel wall, and with a surface of the proximal retainer facing the outer side of the vessel wall.

4. The method of claim 3, wherein the proximal retainer and the distal retainer are each generally circular in shape.

5. The method of claim 4, wherein the proximal retainer has a diameter greater than that of the distal retainer.

6. The method of claim 1, wherein the pushing step (c) comprises the step of pushing the plug through the passageway of the sleeve with the positioning tool until a predetermined location of the positioning tool reaches a proximal end of the sleeve.

7. The method of claim 1, wherein the mating step (a) comprises the step of making a knob at a distal end of the positioning tool with a socket of the plug.

8. The method of claim 1, wherein the sleeve is a catheter sheath introducer.

9. The method of claim 1, wherein the plug comprises a biodegradable material.

\* \* \* \* \*

UNITED STATES PATENT AND TRADEMARK OFFICE
CERTIFICATE OF CORRECTION

PATENT NO.: 5,690,674

DATED: November 25, 1997

INVENTOR(S): Roberto Diaz

It is certified that error appears in the above-identified patent and that said Letters Patent is hereby corrected as shown below:

Claim 7, line 2 (Column 6, line 58), "making" should read -- mating --.

Signed and Sealed this

Thirteenth Day of January, 1998

Attest:

BRUCE LEHMAN

Attesting Officer

Commissioner of Patents and Trademarks